United States Patent [19]

Metzner et al.

[11] Patent Number: 4,662,208

[45] Date of Patent: May 5, 1987

[54] APPARATUS FOR THE DRAWING OFF OF UNTREATED AND TREATED DIALYZING LIQUID AND/OR BLOOD FROM A DIALYSIS DEVICE

[75] Inventors: Klaus Metzner, Bad Homburg; Detlef Westphal, Oberursel; Wolfgang Allendörfer, Bad Homburg; Reinhard Hahnel, Lollar; Hans-Dietrich Polaschegg, Oberursel, all of Fed. Rep. of Germany

[73] Assignee: Fresenius AG, Fed. Rep. of Germany

[21] Appl. No.: 732,025

[22] Filed: May 8, 1985

[30] Foreign Application Priority Data

May 8, 1984 [DE] Fed. Rep. of Germany ....... 3416956

[51] Int. Cl.$^4$ ..................... B01D 13/00; B01D 31/00; G01N 33/49
[52] U.S. Cl. ..................... 73/1 R; 422/68; 422/81; 436/178; 210/321.3; 210/96.2
[58] Field of Search ............... 604/4, 5, 6; 73/864.81, 73/1 R; 210/96.2, 321.2, 321.3; 422/68, 81, 82; 436/8, 16, 178

[56] References Cited

U.S. PATENT DOCUMENTS

| | | | |
|---|---|---|---|
| 3,241,923 | 3/1966 | Ferrari | 73/864.81 X |
| 3,441,136 | 4/1969 | Selfuss et al. | 210/321.3 X |
| 3,490,591 | 1/1970 | Jones et al. | 210/321.3 X |
| 3,722,680 | 3/1973 | Smith | 210/96.2 |
| 3,926,561 | 12/1975 | Lucero | 436/178 |
| 4,119,406 | 10/1978 | Clemens | 422/81 |
| 4,123,353 | 10/1978 | Håkansson et al. | 210/96.2 X |
| 4,127,111 | 11/1978 | Drolet | 422/81 X |
| 4,230,601 | 10/1980 | Hill | 436/8 X |
| 4,430,098 | 2/1984 | Bowman et al. | 210/321.3 X |
| 4,508,622 | 4/1985 | Polaschegg et al. | 210/96.2 |
| 4,554,069 | 11/1985 | Aid et al. | 210/321.2 X |

FOREIGN PATENT DOCUMENTS

| | | | |
|---|---|---|---|
| 2140677 | 2/1973 | Fed. Rep. of Germany | 210/321.3 |
| 2419516 | 12/1974 | Fed. Rep. of Germany | 210/321.2 |
| 2522180 | 11/1976 | Fed. Rep. of Germany | 210/321.3 |
| 2921767 | 1/1980 | Fed. Rep. of Germany | 422/81 |
| 216630 | 12/1984 | German Democratic Rep. | 210/321.3 |
| 1332143 | 7/1973 | United Kingdom | 210/321.3 |

OTHER PUBLICATIONS

"Transmembrane Pressure Stabiliser for Haemodialysis"; *Biomedical Engineering;* Jun. 1976; 3 page reprint; Gusuke Anno et al.

Primary Examiner—Michael J. Tokar
Assistant Examiner—Tom Noland
Attorney, Agent, or Firm—Andrus, Sceales, Starke & Sawall

[57] ABSTRACT

An apparatus (1) for the drawing off of untreated and treated dialyzing liquid and/or blood from a dialysis device (1) has a dialyzer, from which a first line (22) goes off upstream and a second line (24) goes off downstream, which join into a third line (54). The third line (54) is connected to an analysis device (57). In each of the first and second lines is provided a pump (26, 28) and a shut-off element (56, 56'), between which an overflow (38, 40) per line is arranged. This on the one hand ensures that the liquid in the lines (22, 24) are kept constantly in motion, which prevents the formation of line blockages in the case of liquids tending to coagulate, and on the other hand considerably reduces the displacement time of the liquid to be investigated to the analysis device (57).

13 Claims, 5 Drawing Figures

APPARATUS FOR THE DRAWING OFF OF UNTREATED AND TREATED DIALYZING LIQUID AND/OR BLOOD FROM A DIALYSIS DEVICE

BACKGROUND OF THE INVENTION

1. Field of the Invention

The invention relates to an apparatus for the drawing off of untreated and treated dialyzing liquid and/or blood from a dialysis device.

2. Description of the Prior Art

Such an apparatus of this generic type is known for example from U.S. Pat. No. 4,508,622. The dialysis device of this known apparatus has a dialyzer from which a first line goes off upstream and a second line goes off downstream. These two lines join into a third line which is connected to an analysis device. The first and second lines are each provided with a shut-off element as well as with at least one pump for displacement of the liquid in the lines.

However, what is disadvantageous first of all in this known apparatus is that if a line is shut down by closing the corresponding shut-off element, a residual amount of liquid is left in the line which, in the case of liquids such as blood in particular, tends to coagulate due to lack of movement, which blocks the line. Furthermore, the arrangement of the shut-off elements in the direct vicinity of the main line results in the disadvantage that, when opening one of the shut-off elements, if a measurement of untreated or treated liquid is to be carried out, this liquid has to flow along a long flow path to the analysis device as the pump is arranged in the third line and must therefore displace the liquid to be investigated practically directly from the relatively distant main line to the analysis device. This results in undesirably long delays before an analysis cycle can be initiated.

SUMMARY OF THE INVENTION

It is therefore the object of the invention to create an apparatus for the drawing off of untreated and treated dialyzing liquid and/or blood from a dialysis device of the general type described above which makes possible both the avoidance of blockages in the lines leading to the analysis device and the avoidance of undesirably long displacement times of the liquid to be investigated to the analysis device.

This and other objects are achieved by the provision of a pump in each of the first and second lines and an overflow in each case between pumps and shut-off elements. Through this, it is achieved on the one hand that the liquid in the lines can be kept constantly in circulation which, without further aids, prevents a coagulation in the liquids and thereby a blockage of the lines. On the other hand however, by these measures it is also achieved that the liquid to be analyzed is constantly available in the current state directly in the vicinity of the analysis device so that, after opening the respective shut-off element, there is only a short flow path still to be covered from the overflow to the analysis device, so that an analysis without great time delay can be carried out shortly after opening the respective shut-off element.

BRIEF DESCRIPTION OF THE DRAWING

Further details, features and advantages of the invention are disclosed by the following description of exemplary embodiments with reference to the drawing in which.

DESCRIPTION OF THE PREFERRED EMBODIMENTS

Figure 1:
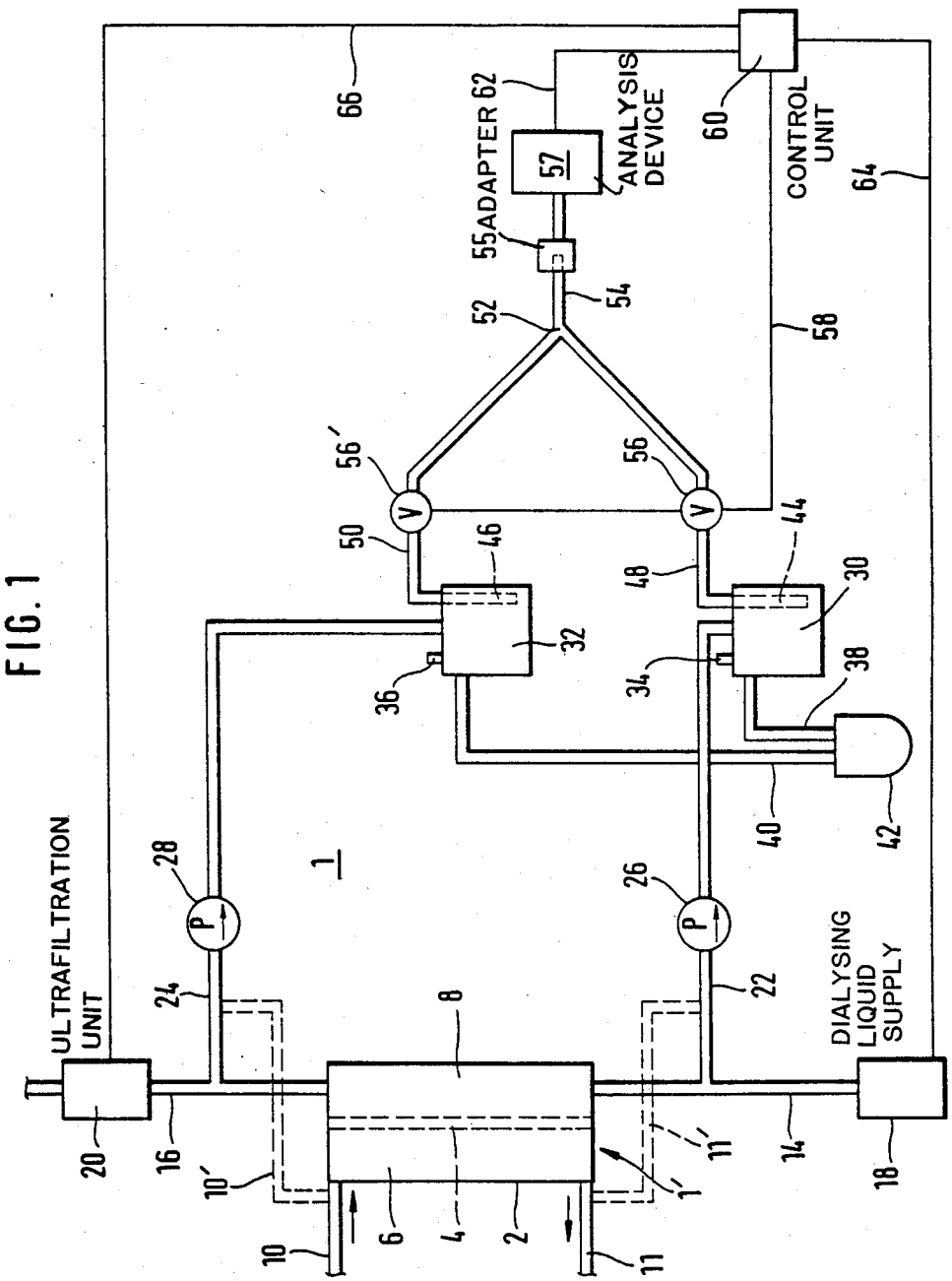
FIG. 1 shows a first embodiment of the apparatus according to the invention.

FIG. 1 illustrates an apparatus 1 for the drawing off of untreated and treated dialyzing liquid and/or blood from a dialysis device 1'.

The dialysis device 1' consists substantially of a dialysis filter 2, which has a semipermeable membrane 4 which divides the dialysis filter into two chambers 6 and 8 separate from each other.

The chamber 6 has a supply line 10 and a discharge line 11 for a first liquid, preferably blood, while the second chamber 8 has a supply line 14 and a discharge line 16 for a second liquid, preferably for the dialyzing liquid.

In this arrangement, the supply line 14 is connected to an apparatus 18 for the provision of fresh dialyzing liquid, while the discharge line 16 downstream of the dialysis filter 2 is connected to a unit 20 for displacement of the dialyzing liquid through the dialysis filter 2 and for generation of an ultrafiltrate. This unit 20 may also be divided up into a pure displacement apparatus and an ultrafiltrate pump.

According to the embodiment illustrated in FIG. 1, directly ahead of and behind the dialysis filter 2 branch a first and a second line 22 and 24, respectively, into each of which are interposed pumps 26 and 28, respectively, which are preferably peristaltic tube pumps.

Figure 4:
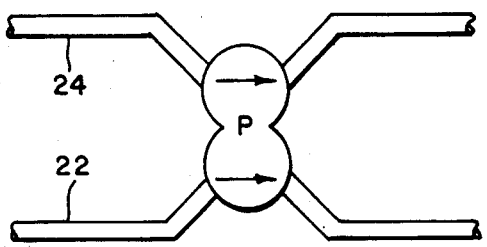
FIG. 4 shows a double channel pump suitable for use in the present invention.

The pumps 26 and 28 may however in this case also be designed as twin tube pumps, sometimes called double-tube or double-channel pumps, which in the conventional manner of such pumps each apply pump pressure to the line 22 and the line 24. See FIG. 4.

The lines 22 and 24 each open out into a drop chamber 30 and 32, respectively, which are preferably of miniaturized design and have a capacity of about 0.2 to 1 ml. These drop chambers 30 and 32 each have venting pipes 34 and 36 on the upper side and can thereby be kept at normal pressure. Furthermore, in the vicinity of the upper edge, overflow lines 38 and 40, respectively, branch off, opening into a bag 42.

Inserted in the drop chambers 30 and 32 down almost as far as the bottom are pipe pieces 44 and 46, respectively, which outside the drop chambers 30 and 32 are in connection with lines 48 and 50, respectively, which come together at 52 and merge into a third line 54. This line 54 is fitted into an adapter 55. This adapter 55 is in turn part of an analysis device 57, the design of which is described in U.S. patent application Ser. No. 732,022, filed May 8, 1985, by the same applicant and to the complete contents of which reference is made.

Figure 5:
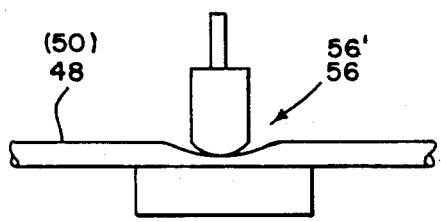
FIG. 5 shows a clamp or clip mechanism suitable for use in the present invention.

The lines 48 and 50 can be closed and opened alternately by a shut-off element 56 and 56', respectively, see FIG. 5., so that either the drop chamber 30 or the drop chamber 32 is connected to the analysis device 57.

The shut-off elements 56 and 56', designed in the case of this example as double clips, are connected via a line 58 to a control unit 60, which receives its time cycle via a line 62 from the analysis device 57.

It is advantageous if the dead volume formed by the lumina, i.e. cavities, of the tubular lines 48, 50 and 54 is as small as possible and is, in the case of this example, at most about 0.2 to 0.3 ml. In the analysis by the analysis device 57, this is taken into account by a pump of the analysis device 57 being actuated for a correspondingly long time so that in each case the liquid directly in the drop chambers 30 and 32, respectively, passes into a measuring or flow channel of the analysis device 57 and is measured there.

As already explained above, the entire system is pressure-equalized by the venting pipes 34 and 36, so that no underpressures occur which can disturb the operation of the analysis device 57.

The pumps 26 and 28 displace dialyzing liquid constantly from the dialysis circuit formed by the lines 14 and 16. The length of the lines 22 and 24 does not play any significant part here. The pump rate itself is preferably in a range from 0.1 to 1 ml/minute and does not substantially have any effect on the ultrafiltration rate of the dialysis device 1.

The apparatus illustrated in FIG. 1 is operated as follows:

The pumps 26 and 28, respectively, constantly displace fresh and used dialyzing liquid, respectively, from the lines 14 and 16, respectively, into the drop chambers 30 and 32, respectively. It is ensured here that, at the moment of displacement of the liquid out of the drop chambers 30 and 32, there is always an adequate quantity of liquid available, which is ensured by the overflow into the bag 42. The analysis device 57 alternately draws the untreated or treated dialyzing liquid by a corresponding control of the shut-off elements 56 and 56' designed as double clips but which incidentally may also take the form of two separate clips.

The parameters established in the analysis device 57 are indicated there and may be used for control of the apparatus 18 for the provision of dialyzing liquid and/or of the apparatus 20 for generation of the ultrafiltration and for pumping round the dialyzing liquid. For this purpose, the apparatuses 18 and 20 are connected via lines 64 and 66, respectively, to the control unit 60.

Correspondingly, the apparatus 18 can thus be made to generate a dialyzing liquid of other composition, for example a dialyzing liquid with increased or reduced sodium ion content, provided that a reduced or increased sodium level occurs at the output of the dialysis filter 2.

On the other hand however, the ultrafiltration apparatus 20 can also be controlled directly via the concentration of ions in the dialyzing liquid, if it is assumed that the diffusion of the ions through the membrane 4, which are measured in the analysis device 57, can be neglected, in other words there is a balance of ions on either side of the membrane 4. The ultrafiltrate thereby causes the concentration of ions in the dialyzing liquid downstream of the dialysis filter 2 to become less, with the consequence that the concentration can be used to determine and control the ultrafiltration quantity.

The embodiment of the apparatus 1 according to the invention, illustrated in FIG. 1, can of course also be used for relative measurement in blood. This is made possible by the lines 22 and 24 not being connected to the lines 14 and 16, but rather to the lines 10' and 11' illustrated by broken lines in FIG. 1.

In such a case, blood is withdrawn through the entire arrangement and can likewise be measured in the analysis device 57 with respect to its ion concentration and conductivity. The parameters obtained here can also be used for control of the apparatus 18 and/or 20 or else shown visually on a display (not shown) of the analysis device 57.

Incidentally, the measurement can be performed at high speed, i.e. a sample of the dialyzing liquid or of the blood can be withdrawn after about every one to three minutes, while the liquid contained in the other drop chamber runs over into the overflow container or bag, so that there is always a liquid of current composition available for the measurement and this liquid can be delivered to the analysis device 57 without great time delay. Furthermore, the constant flowing of the liquids in the first and second lines 22 and 24, which is ensured by the constantly running pumps 26 and 28, prevents a coagulation and thereby a blockage of the lines 22 and 24, respectively, in all operating states.

Figure 2:
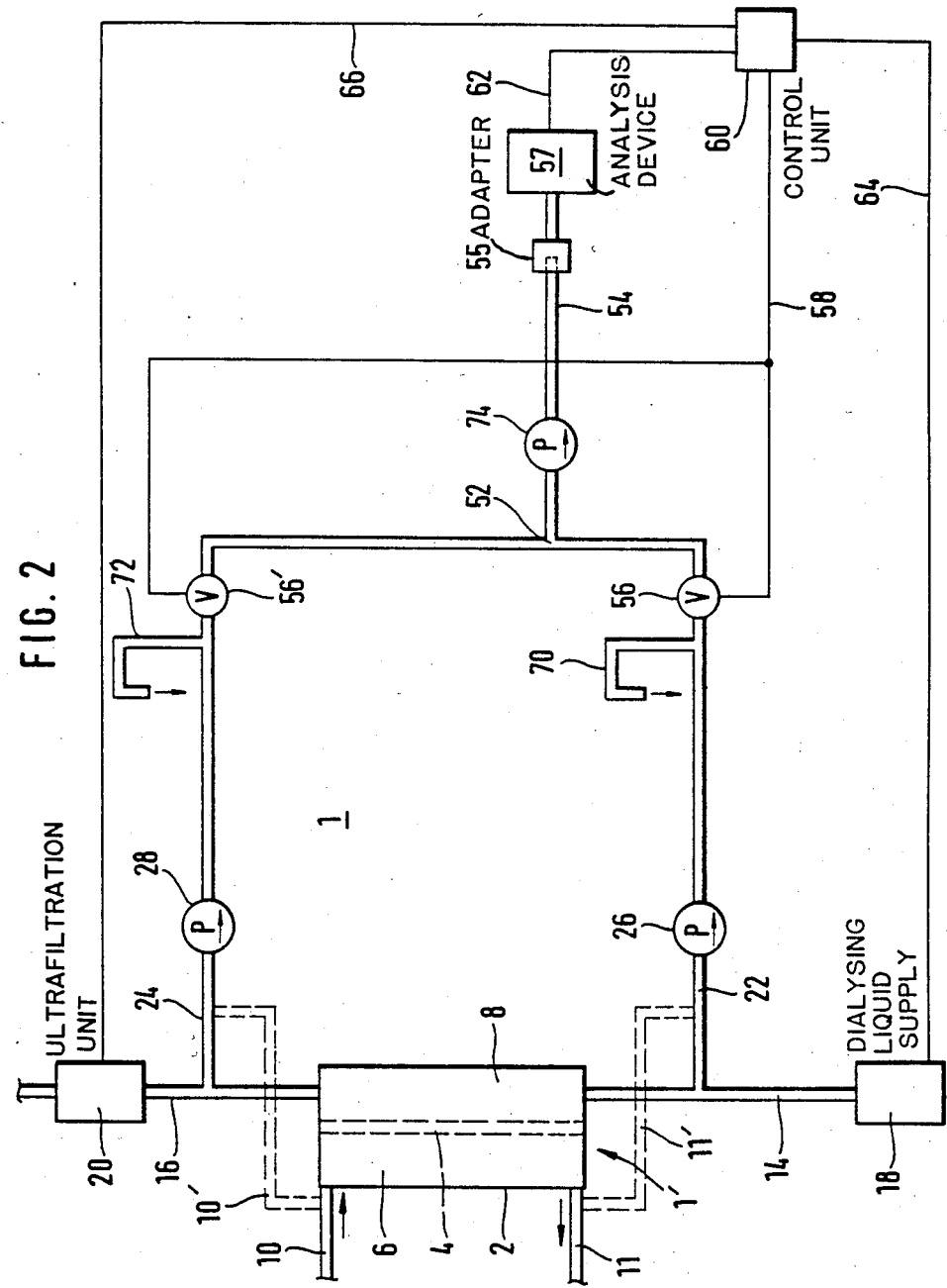
FIG. 2 shows a second embodiment of the apparatus according to FIG. 1.

FIG. 2 illustrates a second embodiment of the apparatus 1 according to the invention, in which all parts which correspond in structure and function to those of the embodiment according to FIG. 1 are denoted by the same reference numbers. Unlike the embodiment according to FIG. 1, the embodiment according to FIG. 2 has in each of the lines 22 and 24, respectively, an overflow 70 and 72, respectively, which is arranged ahead of the shut-off elements 56 and 56'. This construction is advantageous as it makes possible a particularly simple structure. Behind the junction point 52 of the lines 22 and 24 is arranged a further pump 74, which has a lower displacement rate than the displacement rate of the pumps 26 and 28. This ensures that there is always a liquid overflow via the overflows 70 and 72, which in turn prevents air being sucked into the system.

Figure 3:
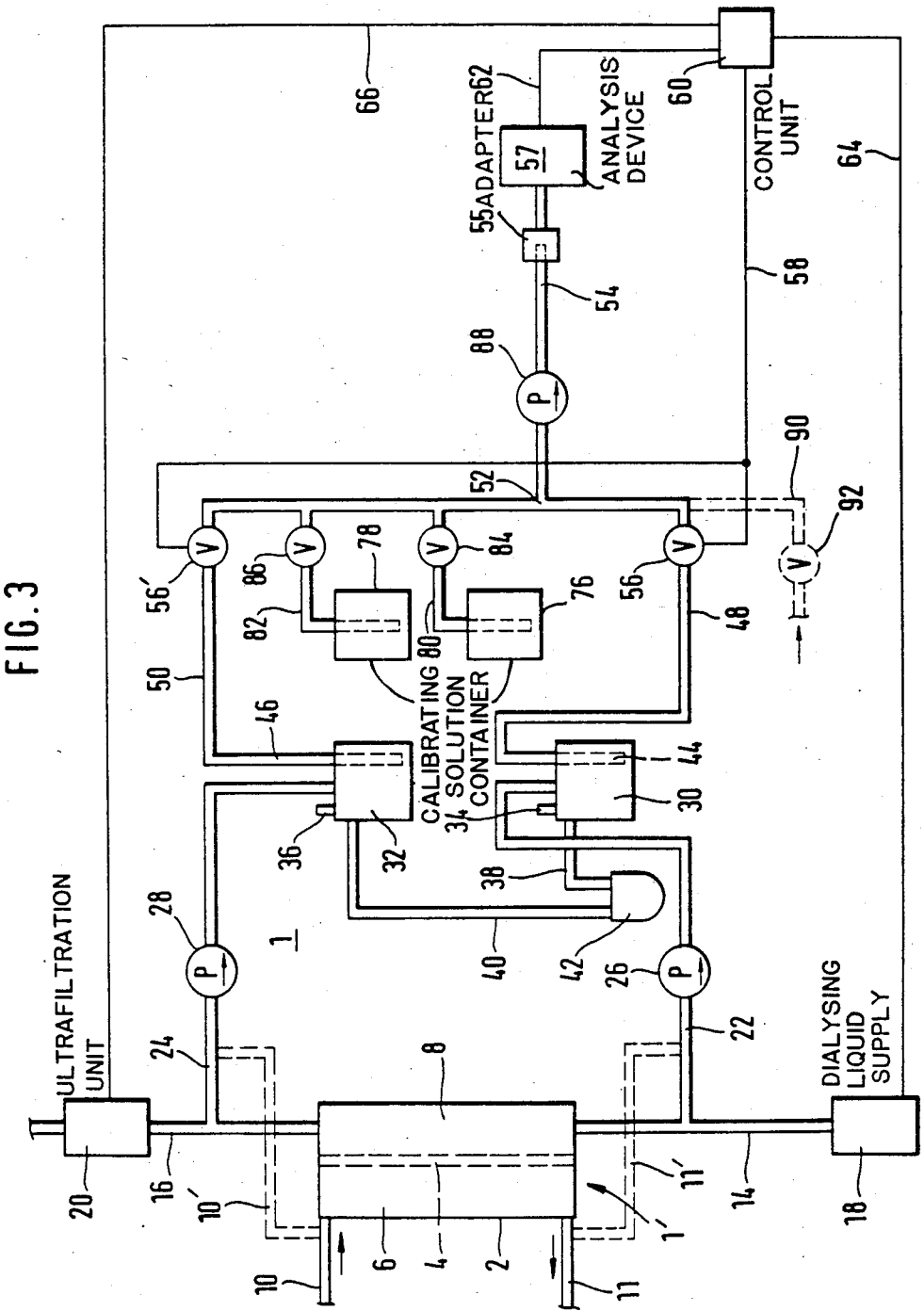
FIG. 3 shows a third embodiment of the apparatus according to FIG. 1.

FIG. 3 illustrates a third embodiment of the apparatus according to the invention, in which again all parts corresponding to FIG. 1 are provided with the same reference numbers.

This embodiment has two additional calibrating solution containers 76 and 78, which are connected to lines 22 and 24. The connection of container 76 is by way of line 80, line 48, pipe piece 44 and drop chamber 30. The connection of container 78 is by way of line 82, line 50, pipe piece 46 and drop chamber 32.

Furthermore, the line 90, drawn in in broken lines, may also be provided and can be connected to the line 22 or else to another point and can be used for sucking air into the system. For this purpose, a controllable shut-off element 92 is likewise fitted in the line 90.

The essence and purpose of this arrangement consists in the fact that it is advantageous to operate the electrode system of the analysis device 57 at constant flow rate and without interruption of the liquid column, in order that the electrode system works as stably as possible. To make a calibration of the zero point and of the gradient of the electode system possible here, the calibrating containers 76 and 78 are provided at the described points and connected via the shut-off elements 84 and 86 to the junction point 52. The pump 88 located behind the junction point 52 displaces calibrating or standard measuring solution through the electrode block of the analysis device 57 into a free outflow, not illustrated in more detail.

In the case of application in hemodialysis, it may be assumed that the composition of the dialyzing liquid upstream of the dialyzer is well known. This dialyzing liquid can thus be used for calibration of the zero point. Only a relative measurement is intended in any case. In general, a mixing system of a dialysis machine is very much more stable than an ion-selective electrode. The gradient of the electrodes can be tested before the start of dialysis by specifically changing the concentration in the dialyzing liquid. It can, furthermore, always be tested whenever the concentration of the dialyzing liquid is changed during hemodialysis due to a control procedure. This may take place, for example, as follows:

Before the start of dialysis, the hemodialysis unit is started up with a concentration of certain electrolyte composition. As soon as a stable concentration state has become adjusted in the dialyzing liquid, which can be established by a usually available monitor in the hemodialysis unit, liquid is withdrawn upstream of the dialyzer and a period is waited until a stable potential has become adjusted at the ion-selective electrodes of the analysis device 57. This potential is read off and stored as zero point. Subsequently the concentration of the dialyzing liquid is increased by a certain amount by a corresponding control of the mixing system of the hemodialysis unit. As soon as a stable state again prevails at the ion-sensitive electrodes, a second potential value is read off and the gradient calculated from the difference between this potential value and the zero point value as well as the difference in concentration. Thus, the ion-sensitive electrodes are calibrated with respect to zero point and gradient.

We claim:

1. An apparatus for drawing off one of dialyzing liquid and blood from a dialysis device, the dialysing liquid and blood being drawn off in the untreated and treated states, said dialysis device having a dialyzer, said apparatus having a first line going off upstream and a second line going off downstream of said dialyzer, which lines join into a third line which is connected to an analysis device of said dialysis device, a shut-off element in both the first line and the second line, a pump (26, 28) in each of the first and (22, 24) for the displacement of liquid in the lines, and an overflow (38, 40) arranged in each of the lines (22, 24) between the pumps (26, 28) and the shut-off elements (56, 56') for permitting the pumps to run continuously.

2. An apparatus as claimed in claim 1, wherein the pumps (26, 28) are designed as double-channel pumps.

3. An apparatus as claimed in claim 1, wherein a pressure-equalizing drop chamber (30, 32) is arranged in each of the first and second lines (22, 24).

4. An apparatus as claimed in claim 3, wherein the drop chambers (30, 32) are provided with overflows (38 and 40, respectively).

5. An apparatus as claimed in claim 4, wherein the overflows are designed as overflow lines (38, 40) which are connected to a collecting bag (42).

6. An apparatus as claimed in one of the claims 3, 4, or 5, wherein each of the drop chambers (30, 32) has passing into it pipe pieces (44 and 46, respectively), from which lines (48 and 50, respectively) branch off which join at a junction point (52), forming the third line (54) which is connected to an adapter (55).

7. An apparatus as claimed in claim 6, wherein a further pump (74) is arranged behind the junction point (52) of the first and second lines (22, 24) in the third line (54), the displacement rate of which pump is less than that of the pumps (26, 28).

8. An apparatus as claimed in claim 6 wherein the shut off elements (56, 56') comprise alternately operable shut off mechanisms and are arranged in lines (48 and 50, respectively).

9. An apparatus as claimed in claim 1, wherein the shut-off elements (56, 56') comprise alternately operable shut off elements.

10. An apparatus as claimed in claim 1 or 9, wherein the shut-off elements (56, 56') are actuated by a control unit (60) of the dialysis device.

11. An apparatus as claimed in claim 1, wherein calibrating solution containers (76, 78), containing calibrating solution, are arranged ahead of the junction point (52) of the first and second lines (22, 24) and which are connected via associated shut-off elements (84, 86) to the first and second lines (22, 24) and wherein a pump (88) for displacement of the calibrating solution is arranged behind the junction point (52) in the third line (54).

12. The apparatus as claimed in claim 1 wherein the shut off elements (56, 56') comprise clamp mechanisms.

13. An apparatus as claimed in claim 1, wherein a further pump (74) is arranged behind a junction point (52) of the first and second lines (22, 24) in the third line (54), the displacement rate of which pump is less than that of the pumps (26, 28).

* * * * *